(12) United States Patent
Yamakawa et al.

(10) Patent No.: US 8,043,561 B2
(45) Date of Patent: Oct. 25, 2011

(54) ANALYZER, CONVEYANCE DEVICE, AND TRANSPORT ANOMALY DETERMINATION METHOD

(75) Inventors: Nobuyoshi Yamakawa, Kobe (JP); Hiroyuki Tanaka, Kobe (JP)

(73) Assignee: Sysmex Corporation, Kobe (JP)

( * ) Notice: Subject to any disclaimer, the term of this patent is extended or adjusted under 35 U.S.C. 154(b) by 1168 days.

(21) Appl. No.: 10/891,980

(22) Filed: Jul. 14, 2004

(65) Prior Publication Data

US 2005/0036913 A1    Feb. 17, 2005

(30) Foreign Application Priority Data

Jul. 17, 2003    (JP) ................................. 2003-198373

(51) Int. Cl.
*G01N 37/00*    (2006.01)
*G01D 11/00*    (2006.01)

(52) U.S. Cl. ................ 422/65; 422/66; 422/67; 422/63; 422/68.1; 436/55; 700/80; 700/79; 700/110; 700/266

(58) Field of Classification Search .............. 422/63–67, 422/99, 100, 102, 50, 62, 68.1; 436/55; 700/80, 700/79, 108, 109, 110, 266
See application file for complete search history.

(56) References Cited

U.S. PATENT DOCUMENTS

| | | | |
|---|---|---|---|
| 4,528,159 A * | 7/1985 | Liston | 422/65 |
| 5,209,903 A | 5/1993 | Kanamori et al. | |
| 5,719,059 A * | 2/1998 | Mimura et al. | 436/50 |
| 6,599,476 B1 * | 7/2003 | Watson et al. | 422/63 |

FOREIGN PATENT DOCUMENTS

| | | |
|---|---|---|
| JP | 06-11057 | 2/1994 |
| JP | 7-239333 | 9/1995 |
| JP | 10-019899 | 1/1998 |
| JP | 11-237384 | 8/1999 |

OTHER PUBLICATIONS

Office Action for Japanese Patent Application No. JP2003-198373.

* cited by examiner

*Primary Examiner* — Jill Warden
*Assistant Examiner* — Cedric Chan
(74) *Attorney, Agent, or Firm* — Brinks Hofer Gilson & Lione

(57) ABSTRACT

Analyzers are described that include a conveyance device for transporting containers which contain analyte, each container having identification information; an identification information reader for reading an identification information of a container transported at a first position by the conveyance device; an analyzer body for acquiring an analyte from a container transported at a second position by the conveyance device and analyzing the analyte; and an anomaly notification device for reporting an anomaly if the identification information reader consecutively reads the same identification information. Conveyance device and transport anomaly determination method are also described.

11 Claims, 8 Drawing Sheets

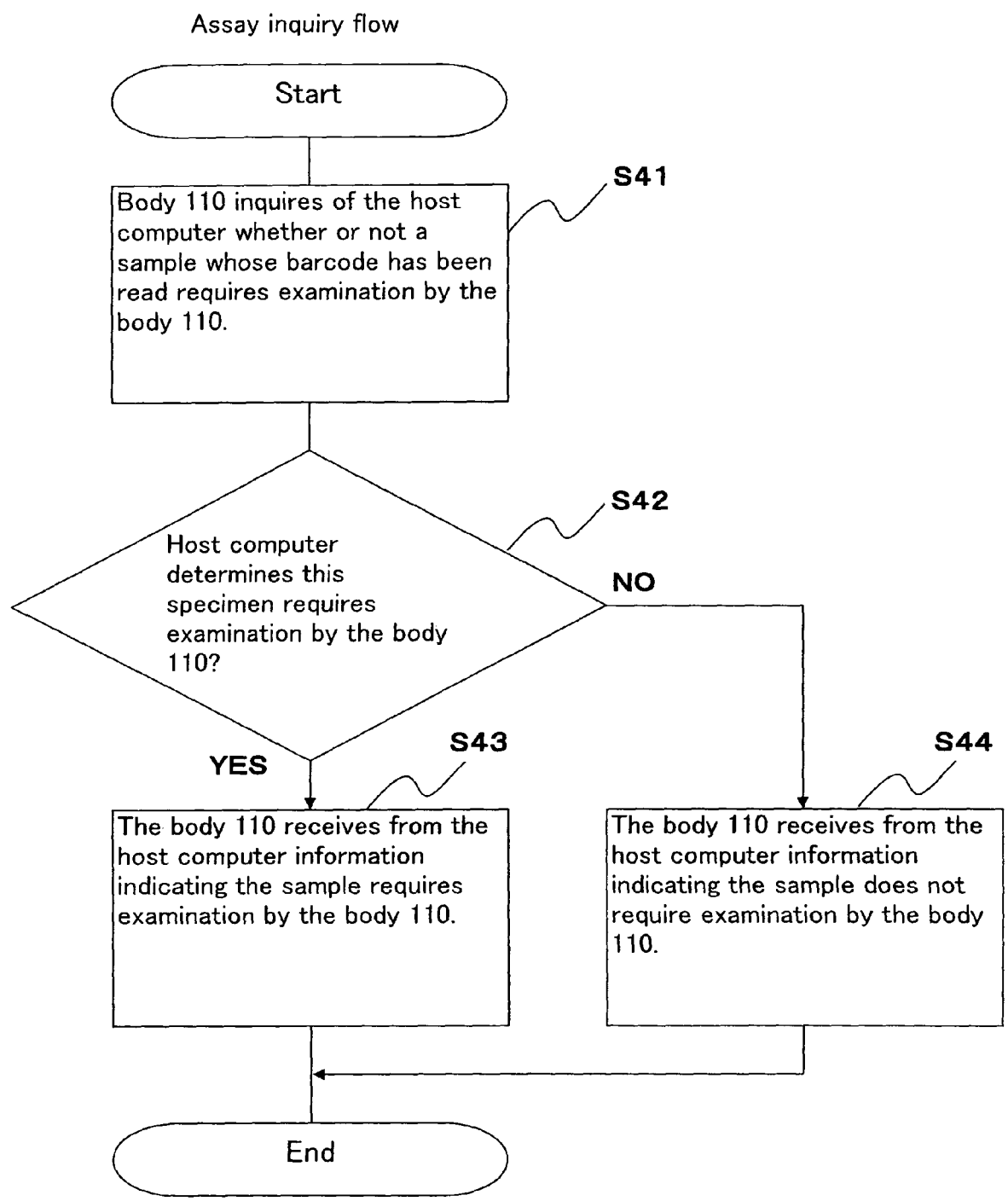

ANALYZER, CONVEYANCE DEVICE, AND TRANSPORT ANOMALY DETERMINATION METHOD

FIELD OF THE INVENTION

The present invention relates to an analyzer including conveyance devices for transporting containers accommodating analyte, a conveyance device, and transport anomaly determination method.

BACKGROUND

Conventionally, analyzing systems which analyze specimens via an analyzer while specimen containers are transported by a conveyance device have become widespread in the effort for more efficient examinations. Specimen inspection systems which read a barcode as identification information from a transported specimen container and subsequently transport the container and suction the specimen are well known as examples of such analyzing systems (for example, refer to Japanese Laid-Open Patent Publication No. 7-239333).

In the specimen inspection system disclosed in Japanese Laid-Open Patent Publication No. 7-239333, each analysis item to be analyzed is determined after a barcode is read and before a sample is suctioned, such that it is possible for the analyzer to quickly suction a sample when the sample container has arrived at the suction position. In this way the examination speed can be increased since the analyzer does not enter a standby state when the suctioning process is performed.

In the specimen inspection system disclosed in Japanese Laid-Open Patent Publication No. 7-239333, however, there are occasions when an anomaly of the conveyance device may occur after the barcode of the transported sample container has been read but before the sample has been suctioned from the sample container whose barcode has been read, such that the sample container remains stopped at the barcode reading position and is not transported; in this case an inconvenience arises inasmuch as the sample container cannot be transported normally. Furthermore, there are occasions when, after the barcode of a sample container being transported has been read but before the sample has been suctioned from the container whose barcode has been read, a user may remove the sample container from the rack and return it one position behind a specific position in the rack, such that the sample container is not transported normally.

When a sample container is not transported normally after the barcode has been read from the sample container being transported but before the sample has been suctioned from the container whose barcode has been read, a problem arises which causes a reduction in the examination reliability inasmuch as a sample accommodated in a sample container which is different than the sample container whose barcode has been read may be erroneously suctioned as the sample of the container whose barcode has been read.

SUMMARY

The scope of the present invention is defined solely by the appended claims, and is not affected to any degree by the statements within this summary.

First analyzer, conveyance device, and transport anomaly determination method embodying features of the present invention improve reliability of examinations.

Second analyzer embodying features of the present invention includes a conveyance device for transporting containers which contain analyte, each container having identification information; an identification information reader for reading an identification information of a container transported at a first position by the conveyance device; an analyzer body for acquiring an analyte from a container transported at a second position by the conveyance device and analyzing the analyte; and an anomaly notification device for reporting an anomaly if the identification information reader consecutively reads the same identification information.

Second conveyance device embodying features of the present invention includes an identification information reader for reading at a first position an identification information of a transport object, each transport object having an identification information; a conveyor for transporting to a second position the transport object whose identification information has been read; and an anomaly notification device for reporting an anomaly if the identification information reader consecutively reads the same identification information.

Second transport anomaly determination method embodying features of the present invention includes a first reading process for reading at a first position an identification information of a transport object, each transport object having an identification information; a transport process for transporting a transport object whose identification information has been read to a second position; a second reading process for reading an identification information from a transport object present at the first position after the transport process has been executed; and an anomaly determining process for determining that an anomaly has occurred during the transport of a transport object if the identification information read in the second reading process is identical to the identification information read in the first reading process.

BRIEF DESCRIPTION OF THE DRAWINGS

FIG. 8 is a flow chart illustrating the assay inquiry operation of the analyzing system of an embodiment of the present invention.

DETAILED DESCRIPTION OF THE EMBODIMENT

The embodiments of the present invention are described hereinafter based on the drawings.

Figure 1:
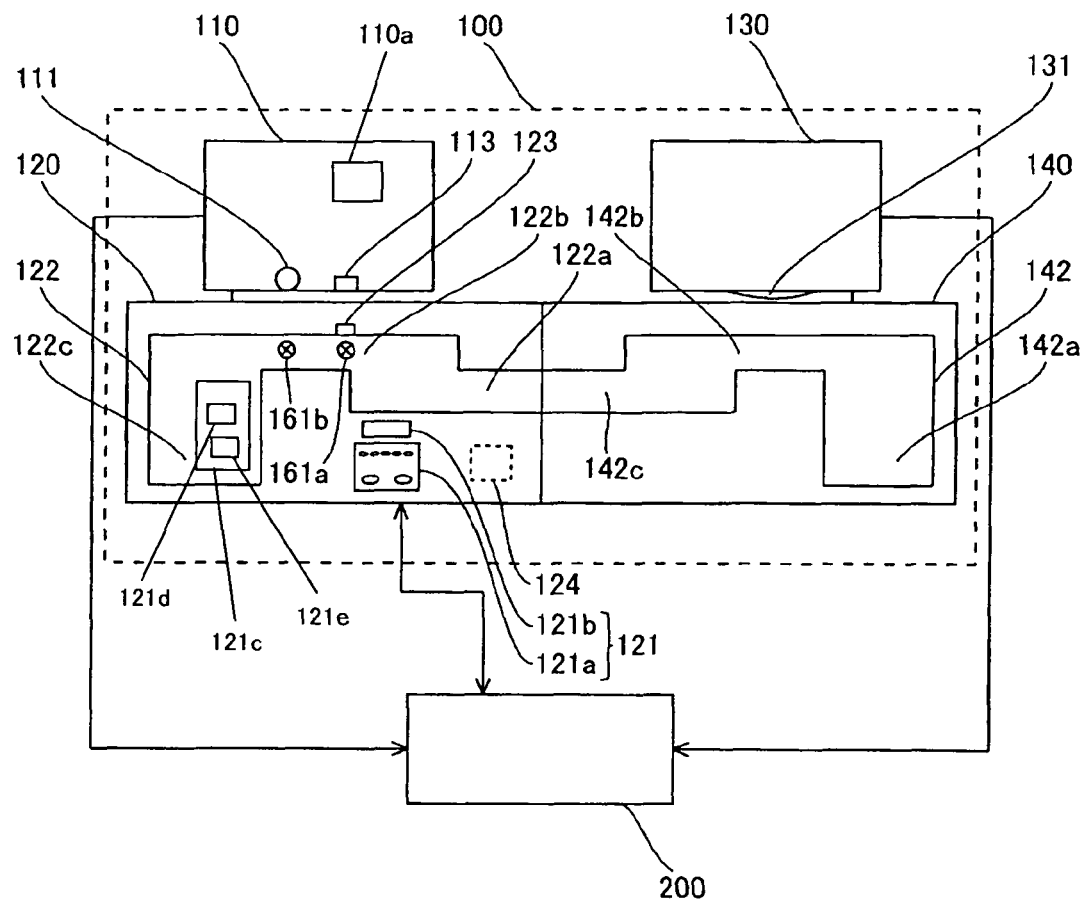
FIG. 1 is a block diagram showing the relationship between the host computer and an analyzing system of an embodiment of the present invention.
Figure 2:
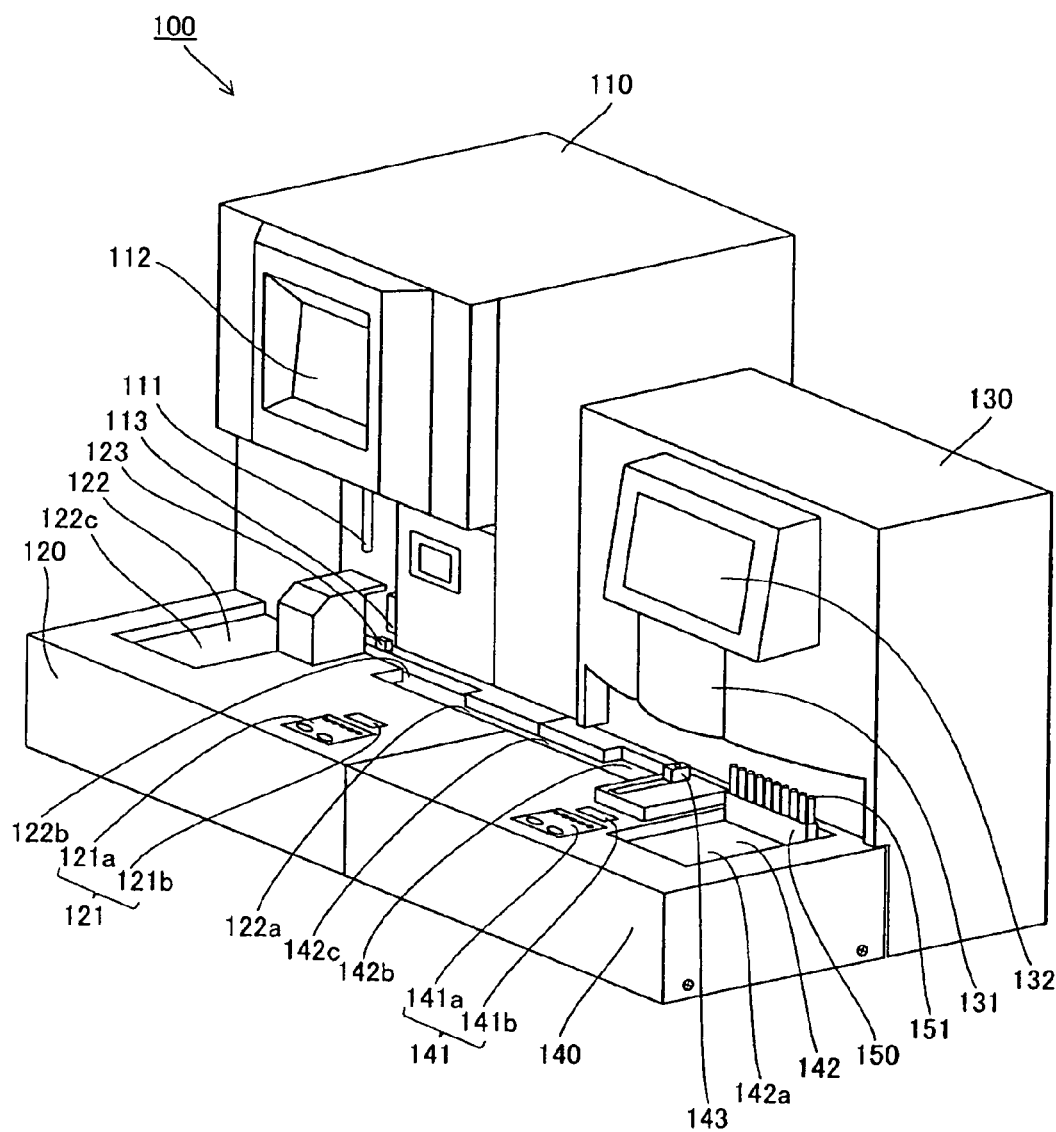
FIG. 2 is a perspective view showing the overall structure of the analyzing system of the embodiment shown in FIG. 1.
Figure 3:
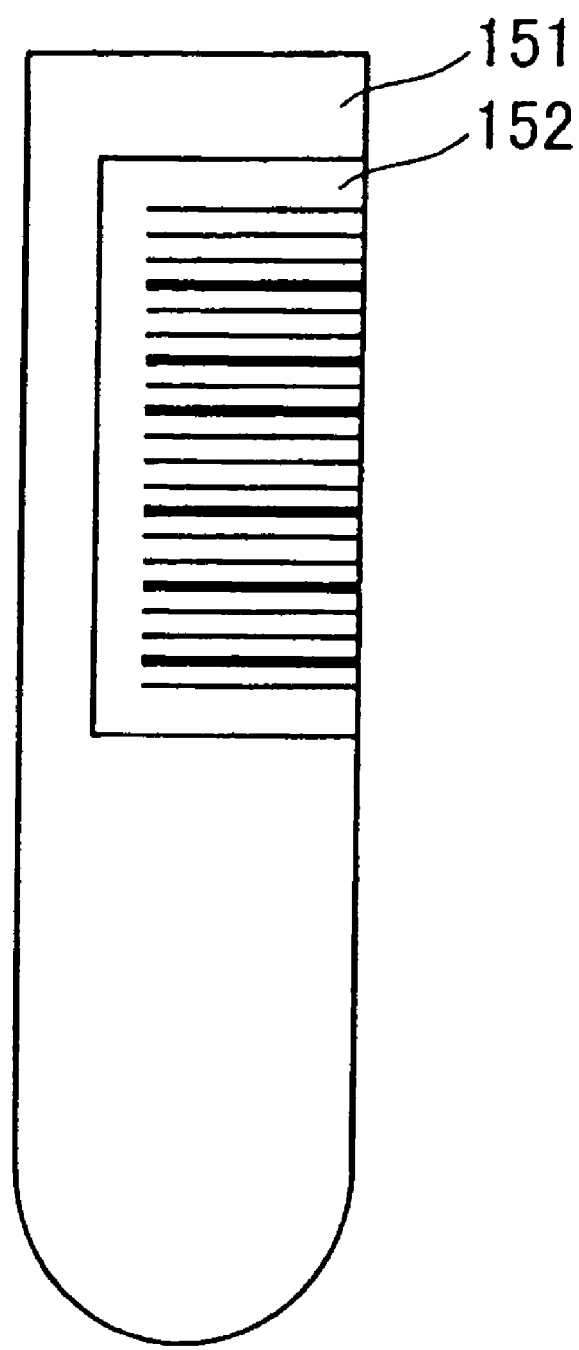
FIG. 3 is a brief illustration showing the sample barcode of a sample container used in the analyzing system of the embodiment shown in FIG. 1.

FIG. 1 is a block diagram showing the relationship between the user side host computer and the analyzing system of an embodiment of the present invention; FIG. 2 is a perspective view showing the overall structure of the analyzing system of the embodiment shown in FIG. 1. FIG. 3 is a brief illustration showing a sample barcode of a sample container used in the analyzing system of the embodiment shown in FIG. 1.

First, the overall structure of the analyzing system 100 of the present embodiment is described with reference to FIGS. 1 through 3. The analyzing system 100 of the present embodiment is provided with a first analyzer including a body 110 and first conveyance device 120, and a second analyzer including a body 130 and a second conveyance device 140.

The body 110 is connected to a user side host computer 200 and the first conveyance device 120, and the body 130 is connected to the user side host computer 200 and the second conveyance device 140. Furthermore, the first conveyance device 120 is connected to the user side host computer 200, body 110, and second conveyance device 140. In addition, the second conveyance device 140 is connected to the body 130 and the first conveyance device 120.

The body 110 and the body 130 of the present embodiment are, for example, urine analyzers. In this case, as shown in FIG. 2, the body 110 is connected to the latter part of the body 130, and is installed to perform analysis and examination more detailed than the urinalysis result of the body 130. The first conveyance device 120 automatically supplies samples to the body 110, and the second conveyance device 140 automatically supplies samples to the body 139. Furthermore, the body 110 includes a controller 110a, a suction unit (assay unit) 111 and display unit 112, as shown in FIGS. 1 and 2. The suction unit 111 is provided to suction a sample accommodated in a sample container 151 which has been delivered to the suctioning position 161b (refer to FIG. 1). The body 130 includes an assay unit 131 and display unit 132, as shown in FIGS. 1 and 2.

In the present embodiment, the suction unit 111 of the body 110 is positioned a predetermined distance on the upstream side of the conveyance device 120, and is provided with a barcode reader 113, as shown in FIGS. 1 and 2. The barcode reader 113 is positioned to read a sample barcode on a sample barcode label 152 adhered to a sample container 151 shown in FIG. 3. A sample number is provided as information included in the sample barcode. The sample numbers are allocated such that each sample has a different number to identify each sample. Furthermore, a sensor (optical sensor) 123 for detecting the presence of a sample container 151 at the barcode reading position 161a is provided at the position of the first conveyance device 120 opposite the barcode reader 113.

In the present embodiment, a setting unit 121 is provided on the first conveyance device 120 for setting the operation of the first conveyance device 120 and displaying the setting content and transport anomaly of the first conveyance device 120. The setting unit 121 includes a key input unit 121a having a plurality of setting keys, and an LCD display unit 121b for displaying the setting content and transport anomaly and the like. Furthermore, the first conveyance device 120 is provided with a controller 121c for storing the setting content and transport anomaly of the first conveyance device 120. The controller 121c includes a memory 121d having a ROM and RAM, and a CPU 121e.

The first conveyance device 120 is provided with a built-in speaker 124 for providing audible notification, such as a beeping sound, when a transport anomaly occurs in the first conveyance device 120.

The first conveyance device 120 is provided with a conveyor 122 for transporting a sample rack 150 holding a plurality of sample containers 151 (ten in the present embodiment) which accommodate samples, as shown in FIGS. 1 and 2. The conveyor 122 includes a transport part 122a, transverse feed part 122b, and collection part 122c. As shown in FIG. 2, the second conveyance device 140 includes a setting unit 141 for setting the operation of the second conveyance device 140, conveyor 142 for transporting a sample rack 150 holding a plurality of sample containers 151 which accommodate samples, and an interrupt sample processing unit 143 used when interrupting the normal sample assay for a special assay. The setting unit 141 includes a key input unit 141a having a plurality of setting keys, and an LCD display unit 141b for displaying the setting content and the like. The conveyor 142 includes a transport part 142a, transverse feed unit 142b, and discharge unit 142c.

Figure 4:
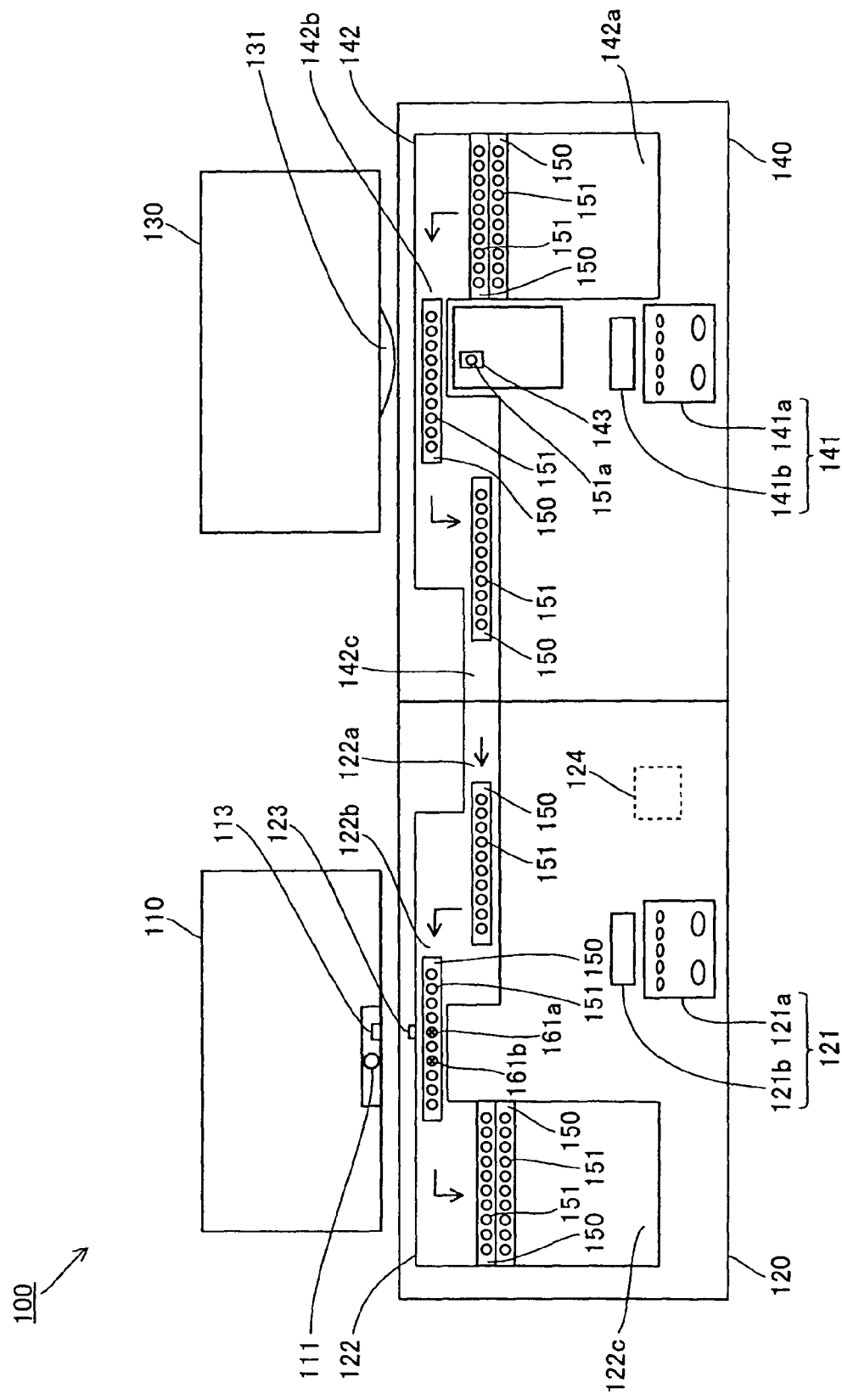
FIG. 4 is a brief illustration of the operation of the analyzing system of the embodiment shown in FIG. 2.
Figure 5:
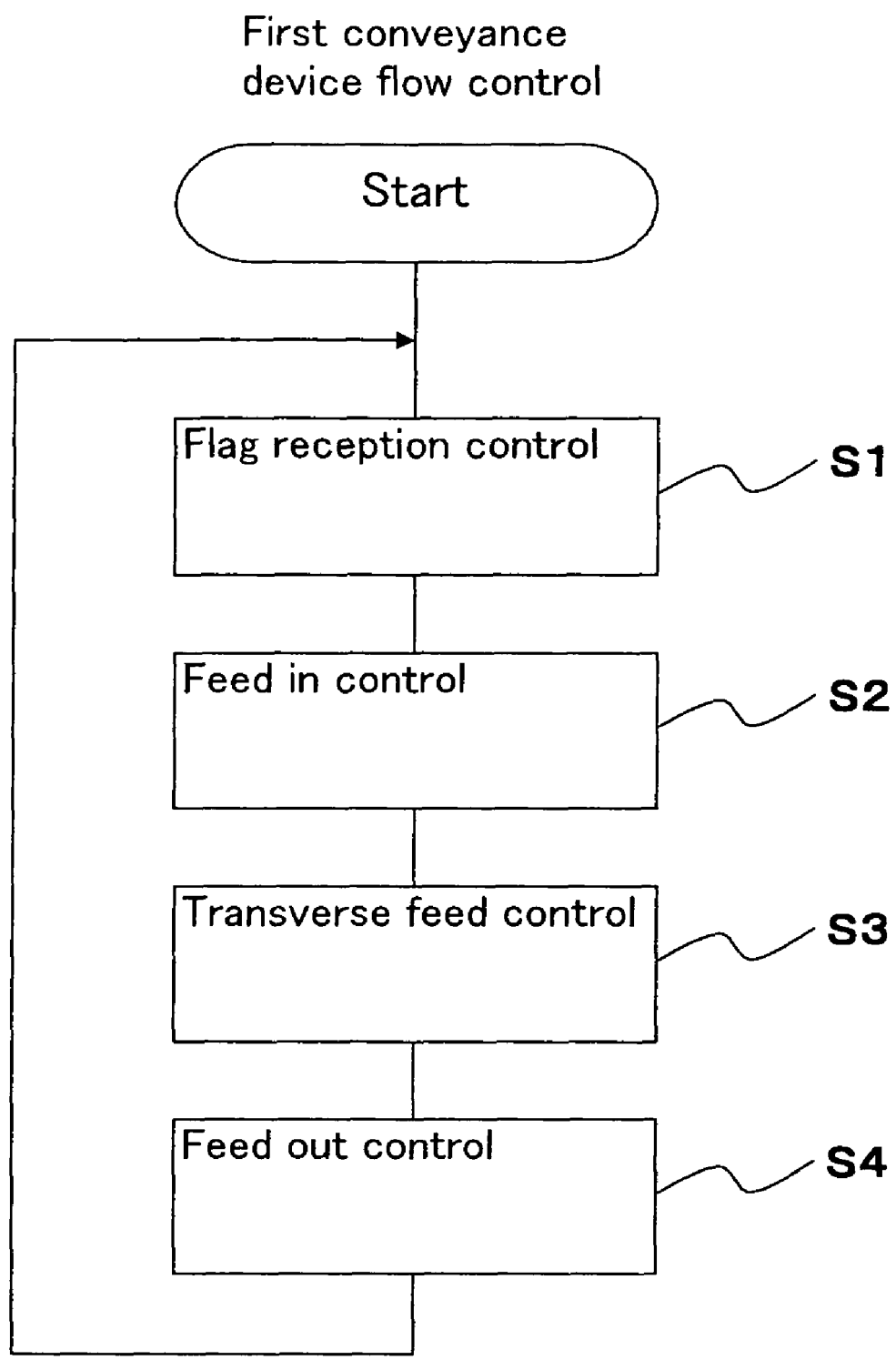
FIG. 5 is a flow chart showing the control flow of a first conveyance device in an analyzing system of an embodiment of the present invention.
Figure 6:
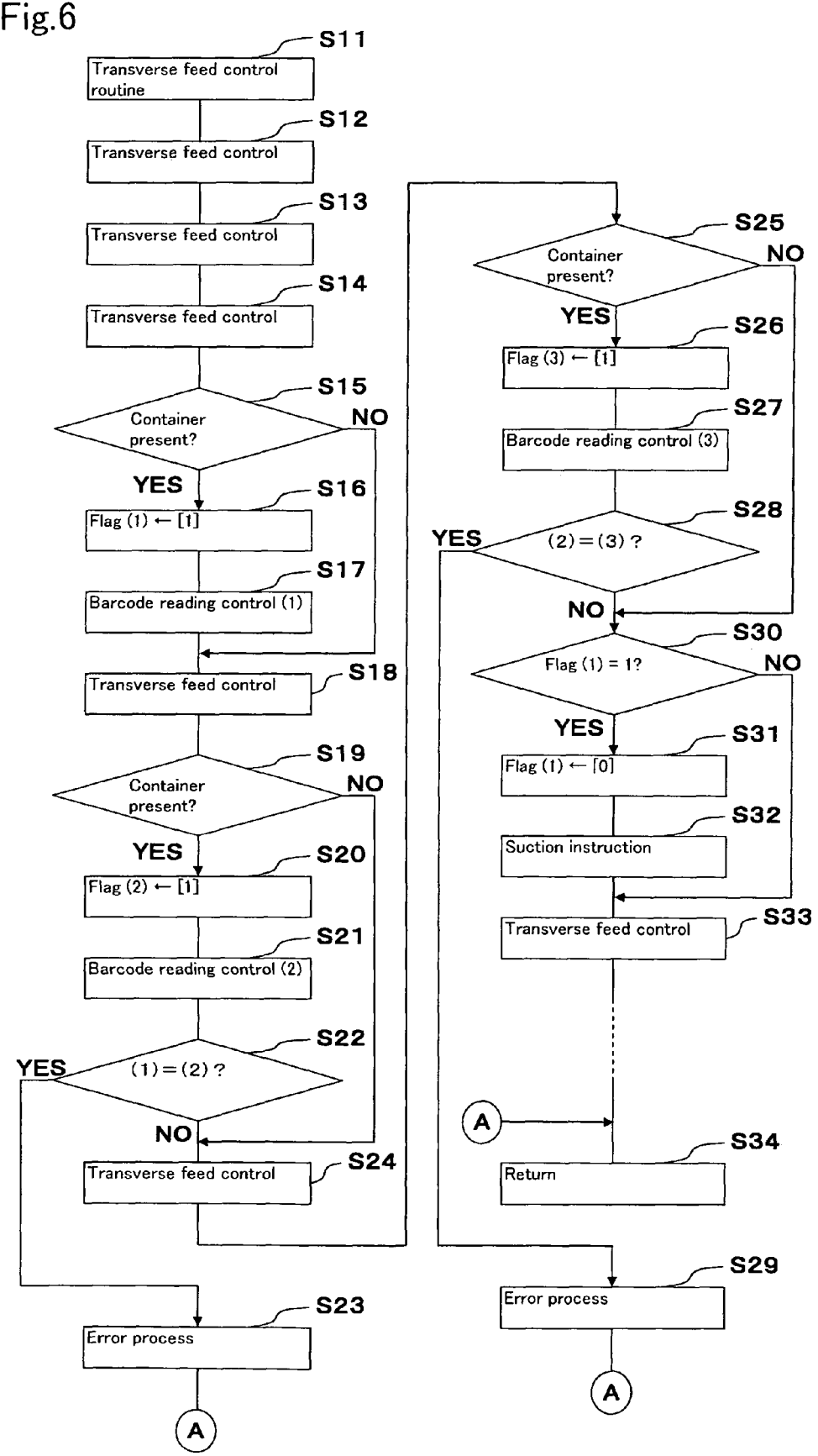
FIG. 6 is a flow chart showing details of the transverse feed control routine shown in FIG. 5.
Figure 7:
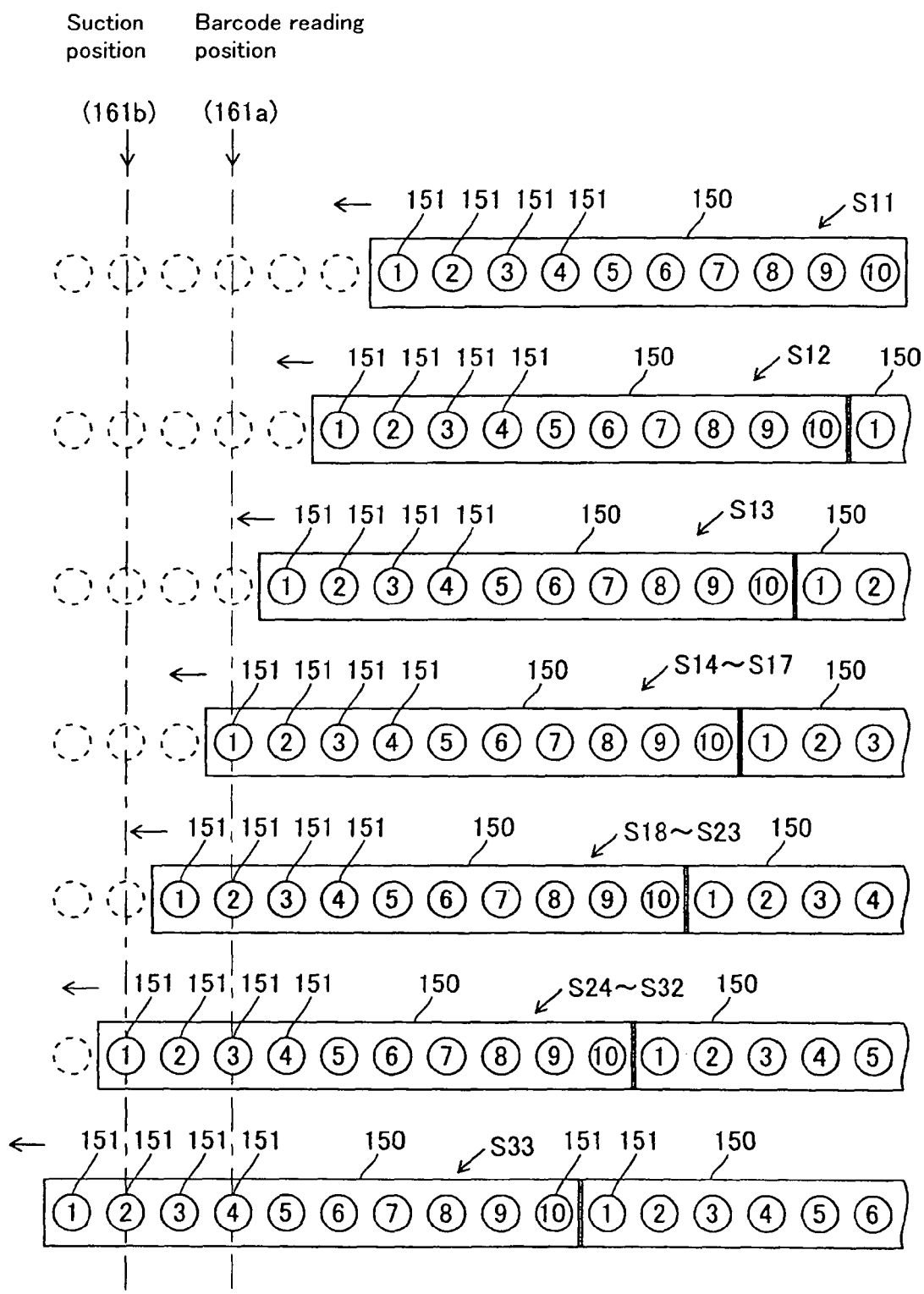
FIG. 7 briefly shows the relationship between the position of the sample container in the sample rack and the suctioning position and the barcode reading position in the transverse feed control routine shown in FIG. 6.

FIG. 4 briefly illustrates the assay operation of the analyzing system of the present embodiment shown in FIG. 2. FIG. 5 is a flow chart showing the control flow of the first conveyance device in the analyzing system of the present embodiment, and FIG. 6 is a flow chart showing details of the transverse feed control in the control flow of the first conveyance device shown in FIG. 5. FIG. 7 briefly illustrates the relationship between the position of the sample container within the sample rack and the barcode reading position and suction position at each step in the transverse feed control routine shown in. FIG. 6. The assay operation of the analyzing system of the present embodiment is described below with reference to FIGS. 1 through 7. The controller 121c runs programs for performing the process shown in the flow charts of FIGS. 5 and 6.

In the analyzing system 100 of the present embodiment, the sample rack 150 holding a plurality of sample containers 151 accommodating samples (urine) is automatically transported in the arrow direction as shown in FIG. 4. Specifically, first, the sample rack 150, which holds a plurality of sample containers 151 accommodating samples, is placed in the transport unit 142a of the second conveyance device 140. Then, the start key is pressed on the setting unit 141. In this way the sample rack 150 placed in the transport unit 142a of the second conveyance device 140 is transported to the transverse feed unit 142b. Then, the sample rack 150 is transported to the assay unit 131 of the body 130 via the transverse feeding of the sample rack 150 one sample container 151 at a time by the transverse feed unit 142b. Next, in the assay unit 131 of the body 130, all the samples accommodated in the sample containers 151 held in the sample rack 150 are sequentially assayed. As shown in FIG. 1, the assay data are transmitted from the body 130 to the host computer 200. Furthermore, after the sample rack 150 is transported from the transverse feeding unit 142b to the discharge unit 142c, the sample rack 150 is transported to the transport unit 122a of the first conveyance device 120.

The first conveyance device 120 detects the sample rack 150 transported to the transport unit 122a, and starts the transport operation in the arrow direction shown in FIG. 4. The operation of the first conveyance device 120 is briefly described below with reference to FIGS. 1, 4 and 5. First, the sample rack 150, which has been transported from the discharge unit 142c of the second conveyance device 140, is received by the transport unit 122a of the first conveyance unit 120 via the rack reception control in step 1 (S1) shown in FIG. 5. Thereafter, the sample rack 150, which has been transported to the transport unit 122a of the first conveyance device 120, is transported to the transverse feed unit 122b of the first conveyance device 120 via the feed control of step 2 (S2). Next, the sample rack 150 is transported to the suction unit 111 of the body 110 by the transverse feeding of the sample containers 151 one container at a time by the transverse feed unit 122b. In the suction unit 111 of the body 110, only the samples determined to require detailed examination by the body 110 are assayed based on the urinalysis results of the body 130. Thereafter, the assay result is transmitted from the body 110 to the host computer 200 (refer to FIG. 1). Then, the sample rack 150 is transported from the transverse feed unit 122b to the collection unit 122c by the feed control in step 4 (S4).

Details of the transverse feed control in the first conveyance device 120 are described below with reference to FIGS. 1, 3, 6, and 7. This control is executed by the controller 121c. First, the start time of the transverse feed control routine in step 11 (S11) shown in FIG. 6 corresponds to the state directly after the end of the feeding of the sample rack 150 from the transport unit 122a to the transverse feed unit 122b of the first conveyance 120. In this case, the first sample container 151 accommodated at the left end of the sample rack 150 is positioned three container spaces in front of the barcode reading position 161a, as shown in FIG. 7. From this state, the sample rack 150 approaches the barcode reading position 161a one sample container 151 space at a time in one cycle of the transverse feed routine in step 12 (S12), as shown in FIG. 7. The first sample container 151 positioned at the left end of the sample rack 150 arrives at the barcode reading position 161a, as shown in FIG. 7, via the transverse feed control executed in step 13 (S13) and step 14 (S14), shown in FIG. 6.

In this state, the sensor 123 (refer to FIG. 1) determines whether or not a sample container 151 is present in step 15 (S15), as shown in FIG. 6. When a sample container 151 is determined to be present in step 15, a flag corresponding to the first sample container 151 is raised in step 16 (S16). This flag is stored in a first region of the memory 121d.

Thereafter, the sample barcode of the sample barcode label 152 (refer to FIG. 3) of the first sample container 151 positioned at the left end of the sample rack 150 is read by the barcode reader 113 (refer to FIG. 1) via the barcode reading control (1) of step 17 (S17). Subsequently, the second sample container 151 from the left end of the sample rack 150 arrives at the barcode reading position 161a, as shown in FIG. 7, via the transverse feed control of step 18 (S18).

When it is determined that the first sample container 151 positioned at the left end of the sample rack 150 is not present in step 15, the sample barcode reading is not performed and the second sample container 151 arrives at the barcode reading position 161a via the transverse feed control of step 18.

Thereafter, the sensor 123 (refer to FIG. 1) determines whether or not a sample container 151 is present at the position of the second sample container 151 from the left end of the sample rack 150 in step 19 (S19). When it is determined that a sample container 151 is present in step 19, then a flag corresponding to the second sample container 151 is raised in step 20 (S20). This flag is stored in a second region of the memory 121d. Then, the sample barcode of the sample barcode label 152 (refer to FIG. 3) of the second sample container 151 is read by the barcode reader 113 (refer to FIG. 1) via the barcode reading control (2) of step 21 (S21).

Next, a determination is made in step 22 (S22) as to whether or not the barcode of the first sample container 151 read in step 17 matches the barcode of the second sample container 151 read in step 21, and when the barcodes match, an error process is executed in step 23 (S23).

The specific content of the error process includes the execution of error notifications via an error display on the LCD display unit 121b of the setting unit 121 and an audible error notification using the speaker 124 shown in FIG. 1, as well as suspending the transport operation of the first conveyance device 120. The error display shown on the LCD display unit 121b may be a displayed message such as, for example, "rack feed error." Furthermore, when the transport of the conveyor 122 of the first conveyance device 120 is suspended, the conveyor 122 does not receive the sample rack 150 even when a sample rack 150 is transported from the conveyor 142 of the second conveyance device 140 to the conveyor 122 of the first conveyance device 120.

When it is determined in step 22 that the sample barcode of the second sample container 151 read in step 21 does not match the sample barcode of the first sample container 151 read in step 17, then a third sample container 151 is delivered to the barcode reading position 161a, as shown in FIG. 7 and the first sample container 151 is delivered to the suction position 161b via the transverse feed control of step 24 (S24). When it is determined that a second sample container 151 is not present in step 19, the sample barcode reading is not performed, and the third sample container 151 is delivered to the barcode reading position 161a, and the first sample container 151 is delivered to the suction position 161b via the transverse feed control of step 24.

In step 25 (S25), the sensor 123 (refer to FIG. 1) detects whether or not a sample container 151 is present at the position which accommodates the third sample container 151 from the left end of the sample rack 150. When it is determined that a third sample container is present in step 25, then a flag indicating the presence of the third sample container 151 is raised in step 26 (S26). This flag is stored in a third region in the memory 121d. Next, the sample barcode of the sample barcode label 152 (refer to FIG. 3) of the third sample container 151 is read by the bar code reader 113 (refer to FIG. 1) via the barcode reading control (3) of step 27 (S27).

In step 28 (S28), a determination is made as to whether or not the barcode of the third sample container 151 read in step 27 matches the barcode of the second sample container 151 read in step 21, and when the barcodes match, the same error process executed in step 23 is executed in step 29 (S29). When it is determined that the sample barcode of the second sample container 151 and ,the sample barcode of the third sample container 151 do not match in step 28, then a determination is made as to whether or not a flag indicating the presence of a first sample container 151 is raised in step 30 (S30). When it is determined that a third sample container is not present in step 25, the barcode reading is not performed and the routine moves to step 30.

When it is determined that a flag indicting the presence of a first sample container 151 is raised in step 30, then the flag stored in the first region of the memory 121d is returned to [0] in step 31 (S31). Then, in step 32 (S32), suction instructions are issued for the first sample container 151 of the sample rack 150 positioned at the suction position 161b (refer to FIG. 7). Thereafter, the second sample container 151 of the sample rack 150 is delivered to the suction position 161b and the fourth sample container 151 is delivered to the barcode reading position 161a via the transverse feed control of step 33 (S33). Subsequently, the same operations of steps 25 through 32 are repeated. After the same controls of steps 25 through 32 have been performed for the tenth sample container 151 of the sample rack 150, then the operations from the transverse feed control routine are repeated via the routine of step 34 (S34) from the first sample container 151 of the next sample rack 150.

Since the flag for issuing the suction instruction is returned to [0] for the first through tenth sample containers 151 of the previous sample rack 150 as described above, the flag can be raised again from the first sample container 151 of the next sample rack 150. Furthermore, since a determination is made as to whether or not the sample barcodes match between the tenth sample container 151 of the previous sample rack 150 and the first sample container 151 of the next sample rack 150, when the barcodes match the same error process as executed in step 23 is executed.

In the present embodiment, an assay inquiry to determine whether or not the body 110 is required to perform an assay is issued after the sample barcode, of the first sample container 151 has been read in step 17 but before the suction instruction has been issued for the first sample container. The assay inquiry operation is described below with reference to FIG. 8. The assay. inquiry operation is performed by the controller 110a of the body 110. First, in step 41 (S41), the body 110 issues an inquiry to the host computer 200 as to whether or not the sample accommodated in the sample container 151 whose barcode has been read requires examination by the body 110. Then, in step 42 (S42), the host computer 200 determines whether or not this sample requires examination by the body 110 based on the assay data transmitted from the body 130.

When it is determined that examination by the body 110 is required in step 42, the body 110 receives from the host computer 200 information specifying that examination is required by the body 110 in step 43 (S43). In this case, the sample is suctioned by the suction unit 111 of the body 110 based on the suction instructions of step 32 shown in FIG. 6.

When the host computer 200 determines that examination of the sample by the body 110 is not required in step 42, then the body 110 receives from the host computer 200 information specifying that examination by the body 110 is not required in step 44 (S44). In this case, the sample is not suctioned by the suction unit 111 of the body 110 even though the suction instruction of step 32 has been issued.

As described above the determination as to whether or not detailed examination by the body 110 is required is made after the barcode has been read at the barcode reading position 161a but before the sample container 151 is delivered to the suction position 161b. In this way the suction unit 111 suctions only the samples determined to require detailed urinalysis by the body 110 among the sample containers 151 delivered to the suction position 161b. Then, sample assay data obtained by the body 110 are transmitted from the body 110 to the host computer 200, as shown in FIG. 1. The assay data transmitted from the body 110 to the host computer 200 do not include graphic data, such as large quantities of scatter data. In this way a concentration of data can be suppressed in the path from the body 110 to the host computer 200, such that when an assay inquiry is issued from the body 110 to the host computer 200, no response or delayed response from the host computer is avoided.

In the present embodiment, when the barcode reader consecutively reads the same barcode, an error message is displayed on the LCD display unit 121b of the setting unit 121 and an audio error notification is issued through the speaker 124, such that a user can easily recognize that a sample container 151 is not transported normally from the barcode reading position 161a to the suction position 161b when an anomaly occurs in the first conveyance device 120 and the sample container 151 remains stopped and is not transported to the barcode reading position 161a, and when a user removes a sample container 151 from the sample rack 150 and erroneously replaces the sample container 151 one position behind the specified position on the rack. Since a user can manage transport anomalies in this way, a sample accommodated in a different sample container 151 than the sample container 151 that was read by the barcode reader is prevented from being erroneously suctioned as the sample of the sample container 151 which was read by the barcode reader. As a result, examination reliability is improved even when the barcode reading position 161a differs from the suction position 161b.

Furthermore, since the transport of the sample container 151 is suspended when the barcode reader 123 has consecutively read the same sample barcode, and the transport of the sample container 151 does not continue when the user is unaware of the notification of an anomaly via the LCD display 121b and the speaker 124, a sample accommodated in a different sample container 151 than the sample container 151 whose barcode was read is not erroneously suctioned as the sample of the sample container 151 whose barcode was read. Examination reliability is thus improved in this way.

In the present embodiment, the standby state of the body 110 can be suppressed by inquiring of the host computer 200 whether or not a sample accommodated in a sample container 151 requires examination while the sample container 151 is being transported from the barcode reading position 161a to the suction position 161b. The examination speed is increased in the body 110 in this way. Furthermore, only samples requiring examination are analyzed by the body 110.

In the present embodiment, the suction operation may not be performed even when the body 110 receives a suction instruction from the first conveyance device 120 depending on the inquiry from the body 110 to the host computer 200 as to whether or not a sample requires examination.

In the present embodiment, the sample barcode of a sample container 151 is accurately read by providing a sensor 123 for detecting whether or not a sample container 151 is present at the barcode reading position 161a.

The disclosed embodiment is in all respects an example and should not be considered as limiting in any way. The scope of the present invention is solely determined by the scope of the claims and not by the description of the embodiment described above, and all modifications included within the scope and equivalent meanings of the claims are included.

For example, although the present embodiment is an example of the present invention applied to an analyzing system including a urine analyzer and a conveyance device, the present invention is not limited to this arrangement, and may be applied to analyzing systems including a conveyance device and other type of analyzer such as a blood analyzer or the like, and analyzing systems including a conveyance device and a smear specimen preparation device. The smear specimen preparation device disclosed in U.S. Pat. No. 6,268,208 may be used as such a smear specimen preparation device.

Although the assay inquiry as to whether or not a sample requires analysis by the body is sent from the body to the host computer in the present embodiment, the present invention is not limited to this arrangement inasmuch as the assay inquiry also may be sent from the first conveyance device to the host computer. In this case, the assay inquiry is also performed after the reading of the sample barcode.

In the present embodiment the barcode reader is provided in the body, however, the present invention is not limited to this arrangement inasmuch as the barcode reader also may be provided in the first conveyance device.

Although a sample barcode is used as an example of sample identification information in the present embodiment, the present invention is not limited to this arrangement inasmuch as identification information other than a barcode, such as an IC chip and the like, also may be used.

In the present embodiment, a speaker is built into the first conveyance device as an example of an anomaly notification device, however, the present invention is not limited to this arrangement, and a speaker built in to the body also may be used as an anomaly notification device.

Although a speaker and LCD display are used as anomaly notification devices in the present embodiment, the present invention is not limited to this arrangement inasmuch as a light source such as a lamp or the like may also be used as an anomaly notification device. In this case, notification of an anomaly may be accomplished by lighting or flashing the lamp.

In the present embodiment, assay data which do not include graphic data such as scatter data are transmitted from the body 110 to the host computer 200, however, the present invention is not limited to this arrangement inasmuch as assay data which include graphic data such as scatter data also may be transmitted from the body 110 to the host computer 200.

Although the analyzer is connected to the body 110 and the first conveyance device 120 in the present embodiment, the present invention also may be applied to an analyzer which integratedly incorporates the first conveyance device 120 into the body 110.

What is claimed is:

1. An analyzer comprising:
   a conveyance device for transporting a rack holding sample containers which contain analyte, each sample container having identification information, wherein the rack holds sample containers in a longitudinal direction thereof, and the conveyance device transports the rack in a predetermined direction straight along the longitudinal direction, such that the sample containers held on the rack are placed at a first position on the conveyance device one by one;
   an identification information reader for reading the identification information on a sample container transported to the first position on the conveyance device;
   an analyzer body for acquiring an analyte from a sample container transported to a second position on the conveyance device and for analyzing the analyte;
   an anomaly notification device for reporting an anomaly; and
   a controller in communication with the conveyance device, the identification information reader and the anomaly notification device, the controller configured for controlling the anomaly notification device to report the anomaly if the identification information reader consecutively reads the same identification information during transport of the rack by the conveyance device,
   wherein the controller controls the conveyance device to transport a container after the identification information reader has read identification information, controls the identification information reader to again read identification information, and controls the anomaly notification device to report the anomaly if the previously read identification information and the subsequently read identification information are identical.

2. The analyzer of claim 1, wherein the anomaly notification device comprises an element selected from the group consisting of a light source, a speaker, a display unit, and combinations thereof; and the anomaly report comprises a notification selected from the group consisting of light from the light source, sound from the speaker, a display of the display unit, and combinations thereof.

3. The analyzer of claim 1 further comprising a sensor for detecting whether or not a container is present at the first position, wherein:
   the controller controls the identification information reader to read the identification information of the container if the sensor detects the presence of the container at the first position.

4. The analyzer of claim 1, wherein the conveyance device comprises the controller.

5. An analyzer comprising:
   a conveyance device for transporting a rack holding sample containers which contain analyte, each sample container having identification information, wherein the rack holds sample containers in a longitudinal direction thereof, and the conveyance device transports the rack in a predetermined direction straight along the longitudinal direction, such that the sample containers held on the rack are placed at a first position on the conveyance device one by one;
   an identification information reader for reading the identification information on a sample container transported to the first position on the conveyance device;
   an analyzer body for acquiring an analyte from a sample container transported to a second position on the conveyance device and for analyzing the analyte;
   an anomaly notification device for reporting an anomaly;
   a controller in communication with the identification information reader and the anomaly notification device, the controller configured for controlling the anomaly notification device to report the anomaly if the identification information reader consecutively reads the same identification information during transport of the rack by the conveyance device; and
   a computer connected to the conveyance device and/or analyzer body, wherein:
   at least one of the conveyance device and the analyzer body inquires of the computer whether or not analysis of an analyte contained in a container is required after the identification information of the container has been read by the identification information reader at the first position and while the container whose identification information has been read is being transported to the second position.

6. The analyzer of claim 5, wherein the analyzer body comprises an analyzer side controller, and wherein the inquiry as to whether or not analysis of an analyte contained in a container is required is transmitted from the analyzer side controller to the computer.

7. An analyzer comprising:
   a conveyance device for transporting a rack holding sample containers which contain analyte, each sample container having identification information, wherein the rack holds sample containers in a longitudinal direction thereof, and the conveyance device transports the rack in a predetermined direction straight along the longitudinal direction, such that the sample containers held on the rack are placed at a first position on the conveyance device one by one;
   an identification information reader for reading the identification information on a sample container transported to the first position on the conveyance device;
   an analyzer body for acquiring an analyte from a sample container transported to a second position on the conveyance device and for analyzing the analyte;
   an anomaly notification device for reporting an anomaly; and
   a controller in communication with the identification information reader and the anomaly notification device, the controller configured for controlling the anomaly notification device to report the anomaly if the identification information reader consecutively reads the same identification information during transport of the rack by the conveyance device, wherein the controller controls the conveyance device to stop the transport of the container if the identification information reader consecutively reads the same identification information.

8. An analyzer comprising:

a conveyance device that transports a rack holding sample containers that contain analyte, each sample container having identification information, wherein the rack holds sample containers in a longitudinal direction thereof, and the conveyance device transports the rack in a predetermined direction straight along the longitudinal direction, such that the sample containers held on the rack are placed at a first position on the conveyance device one by one;

an identification information reader configured to read the identification information on a sample container when transported to the first position by the conveyance device;

an analyzer body configured to acquire an analyte from a sample container transported to a second position by the conveyance device and configured to analyze the analyte;

an anomaly notification device that reports an anomaly; and a controller in communication with the conveyance device, the identification information reader and the anomaly notification device, the controller configured to control the anomaly notification device to report the anomaly if the identification information reader consecutively reads the same identification information at the first position following a conveyance of the sample container from the first position wherein the controller controls the conveyance device to stop the transport of the container if the identification information reader consecutively reads the same identification information.

9. The analyzer of claim 8 where the identification information reader comprises an optical device that reads identification information at only a single position.

10. The analyzer of claim 8 further comprising a second analyzer body separate from the analyzer body comprising an assay unit that assays the analyte after the container is transported to a third position.

11. An analyzer comprising:

a conveyance device for transporting a rack holding a first sample container and a second sample container adjacent to the first sample container which contain analyte, each sample container having identification information;

an identification information reader for reading the identification information of a sample container transported to a first position on the conveyance device;

an analyzer body for acquiring an analyte from a sample container transported to a second position on the conveyance device and for analyzing the analyte;

an anomaly notification device for reporting an anomaly; and a controller in communication with the conveyance device, the identification information reader, and the anomaly notification device, the controller configured for performing successive operations comprising:

(1) transporting the first sample container to the first position;

(2) reading identification information of the first sample container transported to the first position;

(3) implementing an operation of transporting the second sample container to the first position;

(4) reading identification information of a sample container placed at the first position;

(5) controlling the anomaly notification device to report the anomaly if identification information read in (2) is the same as identification information read in (4);

(6) controlling the conveyance device to stop the conveyance of the sample container when an anomaly is reported by the anomaly notification device.

* * * * *